United States Patent
May et al.

(10) Patent No.: US 10,444,118 B2
(45) Date of Patent: Oct. 15, 2019

(54) METHOD FOR ASSESSING A WEAR STATE OF A MODULE OF A TURBOMACHINE, MODULE, AND TURBOMACHINE

(71) Applicant: SULZER MANAGEMENT AG, Winterthur (CH)

(72) Inventors: Frank May, Zurich (CH); Simon Gassmann, Zurich (CH)

(73) Assignee: SULZER MANAGEMENT AG, Winterthur (CH)

( * ) Notice: Subject to any disclaimer, the term of this patent is extended or adjusted under 35 U.S.C. 154(b) by 0 days.

(21) Appl. No.: 14/783,585

(22) PCT Filed: Apr. 25, 2014

(86) PCT No.: PCT/EP2014/058498
§ 371 (c)(1),
(2) Date: Oct. 9, 2015

(87) PCT Pub. No.: WO2014/174097
PCT Pub. Date: Oct. 30, 2014

(65) Prior Publication Data
US 2016/0084734 A1 Mar. 24, 2016

(30) Foreign Application Priority Data

Apr. 26, 2013 (EP) .................................... 13165609

(51) Int. Cl.
*G01M 13/045* (2019.01)
*F04D 15/00* (2006.01)
(Continued)

(52) U.S. Cl.
CPC ....... *G01M 13/045* (2013.01); *F04D 15/0088* (2013.01); *F04D 15/0272* (2013.01);
(Continued)

(58) Field of Classification Search
CPC .. F04D 15/0272; F04D 29/00; F04D 15/0088; G01M 13/045; G01M 13/04;
(Continued)

(56) References Cited

U.S. PATENT DOCUMENTS 4,129,037 A * 12/1978 Toalson ................ G01M 15/00
73/114.77
5,054,938 A 10/1991 Ide
(Continued)

FOREIGN PATENT DOCUMENTS

CN 1382962 A 12/2002
CN 102252843 A 11/2011
(Continued)

OTHER PUBLICATIONS

International Search Report and Written Opinion dated Jul. 16, 2014 in PCT/EP2014/058498 Filed Apr. 25, 2014 (with partial English Translation).

*Primary Examiner* — Octavia Hollington
(74) *Attorney, Agent, or Firm* — Global IP Counselors, LLP

(57) ABSTRACT

A method of evaluating a wear state of an assembly of a flow machine, in particular, of a bearing arrangement of a pump or turbine. For determining a wear characteristic, a mechanical query signal having a pre-definable signal shape is generated by a signal generator and a response signal generated from the query signal is detected using a sensor in contact with the assembly. The response signal is varied in dependence on a variation of a physical operating value of the assembly in accordance with a characteristic pattern, the wear characteristic is determined from the variation of the response signal and the wear state is evaluated using the wear characteristic.

17 Claims, 5 Drawing Sheets

(51) Int. Cl.
  *F04D 15/02* (2006.01)
  *G01L 5/16* (2006.01)
  *G01L 1/16* (2006.01)
  *G01N 3/02* (2006.01)
  *F16C 17/06* (2006.01)

(52) U.S. Cl.
  CPC .............. *G01L 1/165* (2013.01); *G01L 5/167* (2013.01); *G01N 3/02* (2013.01); *F16C 17/06* (2013.01); *F16C 2233/00* (2013.01)

(58) Field of Classification Search
  CPC   G01L 5/167; G01L 1/165; G01N 3/02; F16C 17/06
  USPC ..................................................... 73/774, 777
  See application file for complete search history.

(56) References Cited

U.S. PATENT DOCUMENTS

| | | | | |
|---|---|---|---|---|
| 5,333,240 | A * | 7/1994 | Matsumoto | G01H 1/003 706/20 |
| 5,393,145 | A * | 2/1995 | Ide | F16C 17/035 384/124 |
| 5,630,352 | A * | 5/1997 | Todd | F01B 3/0073 384/2 |
| 6,318,147 | B1 * | 11/2001 | Steinruck | G01D 5/485 73/114.78 |
| 6,484,582 | B2 * | 11/2002 | Ehrfeld | F16C 19/522 384/448 |
| 6,880,379 | B2 * | 4/2005 | Hedberg | G01N 3/30 702/38 |
| 7,582,359 | B2 * | 9/2009 | Sabol | F01D 17/02 428/469 |
| 8,247,949 | B2 * | 8/2012 | Lee | G01N 29/022 310/313 R |
| 8,742,944 | B2 * | 6/2014 | Mitchell | F01D 17/02 340/870.01 |
| 9,400,171 | B2 * | 7/2016 | Kidane | G01B 11/02 |
| 9,702,772 | B2 * | 7/2017 | Haines | G01L 1/165 |
| 2002/0062694 | A1 | 5/2002 | Ehrfeld et al. | |
| 2006/0056959 | A1 | 3/2006 | Sabol et al. | |
| 2013/0315518 | A1 * | 11/2013 | Gassmann | F16C 33/06 384/248 |

FOREIGN PATENT DOCUMENTS

| | | |
|---|---|---|
| CN | 102788695 A | 11/2012 |
| DE | 19950215 * | 6/2001 |
| DE | 10346647 A1 | 5/2005 |
| EP | 0510362 A1 | 10/1992 |
| EP | 1148261 A2 | 10/2001 |
| EP | 2014924 A1 | 1/2009 |
| JP | 07158635 A | 6/1995 |
| RU | 2068553 C1 | 10/1996 |
| RU | 2009106215 A | 6/2007 |

* cited by examiner

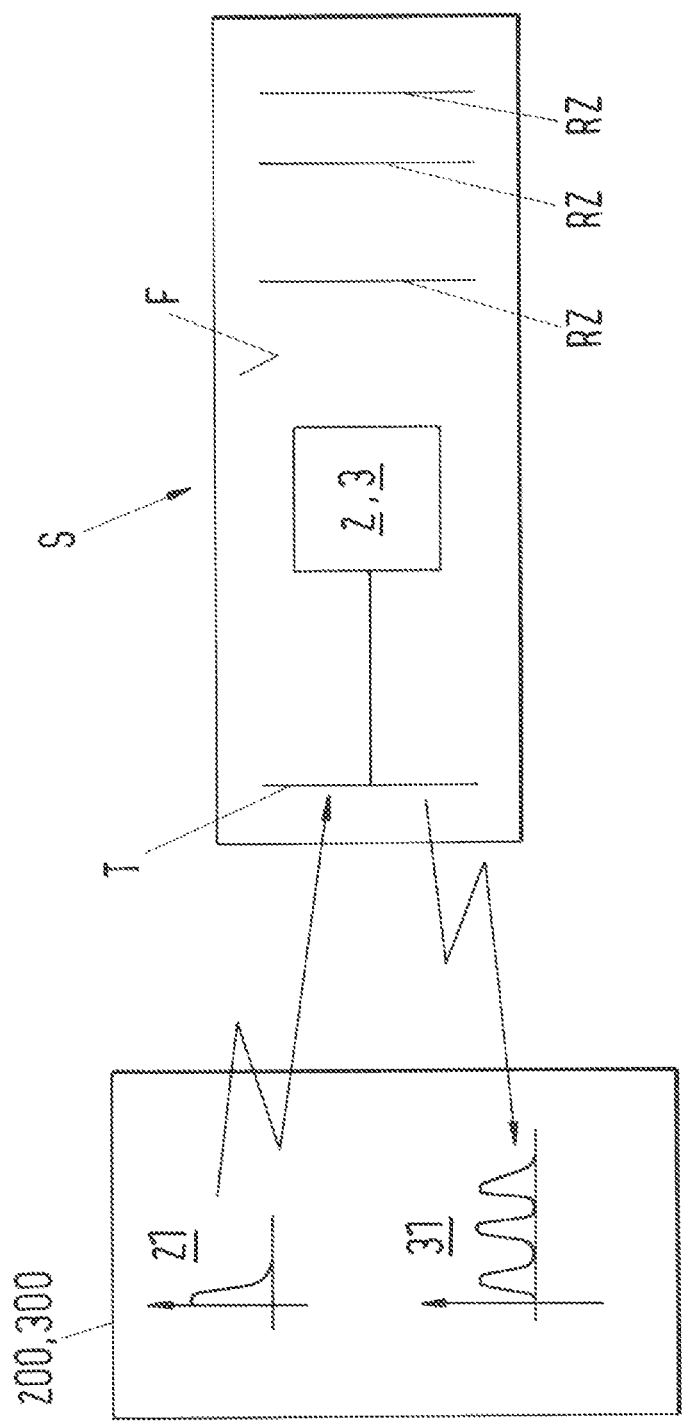

METHOD FOR ASSESSING A WEAR STATE OF A MODULE OF A TURBOMACHINE, MODULE, AND TURBOMACHINE

CROSS-REFERENCE TO RELATED APPLICATIONS

This application is a U.S. National stage application of International Application No. PCT/EP2014/058498, filed Apr. 25, 2014, which claims priority to EP Application No. 13165609.2 filed Apr. 26, 2013, the contents of each of which is hereby incorporated herein by reference.

BACKGROUND

Field of Invention

The invention relates to a method of evaluating a wear state of an assembly of a flow machine, in particular of a bearing arrangement of a pump or turbine, to an assembly of a flow machine as well as to a flow machine, in particular a pump or turbine.

Background Information

Bearings are used everywhere forces acting in specific directions have to be compensated or movements of an object in unwanted directions have to be prevented. In flow machines such as pumps or turbines, two kinds of bearings are essentially used in assemblies having rotating components, namely so-called radial bearings and axial bearings.

The bearings usually used in flow machines are in this respect very frequently assemblies of an extremely complex design in dependence on the specific application whose subcomponents are exposed to different, more or less strong wear mechanisms in operation. This applies both to radial bearings and to axial bearings.

In particular, but not only, mechanical seals and their individual parts are thus wear parts which will fail sooner or later. To delay this for as long as possible and thus to realize service lives which are as long as possible, before a servicing or a replacement of the bearings or their components, such as seals, becomes necessary, a whole number of very different measures are known in the prior art which are familiar to the skilled person per se.

In addition to the radial bearings for taking up radial forces, which in the simplest case can simply comprise a bearing saddle and a shaft which can rotate therein, with the shaft frequently, but not necessarily, being able to be sealed with a shaft seal, for example toward an external atmosphere, so-called axial tilting segment axial bearings are frequently also used for taking up axial forces whose design has long been well-known from the prior art. The general design principle in this respect provides that a plurality of bearing segments in the form of a ring-shaped grouping on a usually metallic carrier body are arranged about a bearing axis in a tilting segment axial bearing and are flooded with a circulating fluid as a lubricant in the operating state. The bearing segments per se comprise a metal, plastic, etc. in dependence on the use and often have the shape of a trapezoidal parallelepiped on whose side facing the carrier body a tilting element is located on which the bearing segment is supported. On the side of the bearing segments remote from the carrier body, a thrust collar is located by which the axial forces of the shaft are transmitted to the bearing, whereby corresponding pressure loads act on the bearing segments. This design principle will be explained even more exactly below with reference to FIG. 3a and FIG. 3b.

When the thrust collar starts to rotate, a shearing of the fluid takes place between the thrust collar and the bearing segments and the thrust collar slides over the bearing segments. The forming of a wedge-shaped hydrodynamic lubricant film, which is an essential component in the operation of the axial bearing arrangement, results in a tilting of each bearing segment since they are supported on a tilting element. The start phase and the stop phase are particularly critical operating ranges for the tilting segment axial bearings, for example in pumps, since very high axial forces act in part in this respect. In these phases, the hydrodynamic lubricant film has not yet fully formed so that the thrust collar and the bearing segment contact one another directly without substantial hydrodynamic lubrication and wear occurs.

The bearing segments are generally mounted loosely and discretely with respect to the carrier body to avoid misalignments and to match the tilting of the bearing segments, which is effected by the formation of the hydrodynamic lubricant film, to the rotating shaft. The loose mounting is in this respect restricted in principle in that the bearing segments have to be held within the arrangement when the shaft does not rotate, that is for example in that the bearing segments are connected to one another by a flexible net or are fastened in a groove at the carrier body by means of a fastening means.

In dependence on the site environment, fluids having a low viscosity are in this respect used in part, for example a water-based lubricant or an oil mixture. In this case, the wear of the bearing segments is not a constant process, but damage to or destruction of the bearing segments often occurs within seconds at high pressure loads.

In this respect, such bearings, just like the radial bearings, are naturally also additionally always exposed to constant wear which finally has the result, even without sudden catastrophic effects, that the bearing or parts thereof have to be repaired or replaced.

In summary, it can thus be stated that in particular the rotating components or those components which are in contact with rotating parts are wear parts which will fail sooner or later. So that such a failure does not occur as a complete surprise, and thus possibly still worse damage is caused to further components of the corresponding machine, it is important already to obtain information on the wear state of a corresponding assembly before the final failure of such a wear part so that the wear state can already be reliably evaluated long before the final failure and preventive measures can possibly be taken.

Only very insufficient measures have previously been known from the prior art to monitor and evaluate the wear state of assemblies of flow machines, for example of bearings or bearing seals or bearing shafts of pumps or turbines or also of tilting segment axial bearings in the operating state.

It is thus known, for example with seals of radial bearings, to observe a leakage flow at the seal which can provide a certain insight into the wear state of the seal or of the corresponding bearing. It is, however, frequently also not possible at all to monitor the leakage flow during the operation of the machine or the information which is obtained by observing the leakage flow is too vague and indefinite to obtain reliable information on the wear state of the corresponding components.

It is in principle also known with both radial bearings and axial bearings, for example, to monitor the temperature of involved construction element components or of bearing fluids such as the temperature of oil which comes into contact with the parts to be monitored for wear in the operating state. This can take place more or less reliably, for example, using thermal elements or using electrical resistance thermometers and in principle allows a good monitoring and evaluation of a wear state of the assembly of interest. However, these methods are as a rule only suitable for laboratory purposes and test purposes since the temperature sensors have to be positioned in a complicated manner, frequently at very inaccessible sites. The measured signals generated by such temperature sensors furthermore have to be connected to corresponding measurement and evaluation instruments via electrical lines so that the use of the aforesaid temperature sensor is in most cases impossible under normal operating conditions across the board as is directly clear to the skilled person.

SUMMARY

It is therefore the object of the invention to provide a reliable method of evaluating a wear state of an assembly of a flow machine which avoids the problems known from the prior art and which is in particular also suitable for use under normal operating conditions across the board and/or in the field, that is also outside the laboratory, for everyday operation. It is furthermore an object of the invention to propose a correspondingly modified assembly of a flow machine as well as a flow machine, in particular a pump or turbine, having such a modified assembly. A method and an apparatus should in particular be provided by the invention so that a reliable monitoring of the wear state is also possible under extreme operating conditions such as with a pump which is installed deep under the sea.

The subject matters of the invention satisfying this object are characterized by a method of evaluating a wear state of an assembly of a flow machine, in particular of a bearing arrangement of a pump or turbine, an assembly of a flow machine, in particular a bearing arrangement of a pump or turbine, and a flow machine, in particular a pump or turbine.

The dependent claims relate to particularly advantageous embodiments of the invention.

The invention relates to a method of evaluating a wear state of an assembly of a flow machine, in particular of a bearing arrangement of a pump or turbine, wherein, for determining a wear characteristic a mechanical query signal having a predefinable signal shape is generated by means of a signal generator and a response signal generated from the query signal is detected using a sensor in contact with the assembly. In accordance with the invention, the response signal is changed in dependence on a variation of a physical operating value of the assembly in accordance with a characteristic pattern, the wear characteristic is determined from the variation of the response signal and the wear state is evaluated using the wear characteristic.

In accordance with the invention, the wear state of the assembly is thus not evaluated as known from the prior art, e.g. using a conventional temperature sensor such as a thermal element or a resistance thermometer. A signal generator is rather used which generates a mechanical query signal from which a response signal is generated, with the response signal being varied in a characteristic manner in dependence on the wear state of the assembly. The response signal is then detected by the sensor so that finally the wear characteristic can be determined from the characteristic pattern variation which the response signal shows in comparison with the query signal and thus the wear state of the assembly or of its components or subcomponents can be evaluated.

Specific examples of sensors used in accordance with the invention are also known per se to the skilled person under the term SAW sensor (surface acoustic wave sensor). Such sensors are preferably manufactured on the basis of a piezoelectric or piezoresistive material which, as is sufficiently known to the skilled person, can generate corresponding electrical signals under the effect of mechanical strains such as stretching, compression, pressure, force, torque, etc. due to its specific crystalline structure. That is, a mechanical strain which a piezoelectric crystal is subjected to, for example, varies its electrical polarization or its charge shift. Conversely, an electrical field applied to the crystal causes mechanical distortion and/or deflection in it.

Due to these properties, piezoelectric materials are also indirectly suitable for temperature measurement or for determining temperature changes with a suitable calibration. A huge advantage of such SAW sensors built up of piezoelectric materials is inter alia the fact that they can be configured as comparatively small, often in dimensions of a few millimeters or even smaller. Since the piezoelectric effect is ultimately due to polarization phenomena in the crystal lattice, such a sensor module can be operated and read out using minimal electrical energy, since the major effect, namely the variation in the polarization or charge shift in the crystal by application of a mechanical voltage or the expansion phenomena of the crystal lattice on the application of an external electrical field takes place almost without current and thus consume practically no electrical energy.

It is therefore possible both to control and operate such sensor modules wirelessly by means of an electromagnetic wave via a suitable antenna and to read them out again wirelessly via an antenna. This has the huge advantage that such sensors do not necessarily have to be wired and can thus also be installed completely without problem into rotating components. The sensor modules can naturally also be wired in special cases.

In this respect, such sensor modules are simultaneously robust, have extremely long service lives and are moreover commercially available directly at very favorable prices from a plurality of manufacturers.

The monitoring of the temperature or the time variation of the temperature in the operating state has proved to be a particularly reliable parameter which is easy to handle for evaluating a wear state of an assembly of a flow machine, in particular for evaluating the wear state of a bearing arrangement or for evaluating the wear state of components or subcomponents such as inter alia of seals at bearing arrangements. Further prominent examples of assembly components which are naturally also covered by the invention are e.g. slide ring seals, seal gaps and other components or subcomponents known to the skilled person, which are at risk of wear and therefore have to be monitored.

If namely the temperature is monitored, preferably in dependence on the time, at suitable points in the assembly, slowly developing damage, for example at a bearing or at a seal of the bearing or at other components or subcomponents of the bearing can, on the one hand, be recognized and monitored at a very early time. If such temperature curves are suitably calibrated to the relative characteristics, a repair or replacement of the bearing can, for example, take place at a very early point in time before the corresponding component finally fails. However, very spontaneous, possibly catastrophic, damage can also be detected practically directly on its arising so that a corresponding machine can, for example, be immediately switched off, or its power can be reduced before worse and additional damage can occur at the corresponding machine.

In this respect, the skilled person easily understands that the monitoring can also in particular be easily automated by an automatic reading out of the sensor units used so that e.g. a corresponding message can be triggered when a service or repair is necessary or, in the worst case, an emergency shut-down or the like can naturally also be automatically initiated.

In this respect, it is possible without problem also to monitor different components or subcomponents simultaneously and independently of one another by positioning a plurality of sensor units at different locations at or in the assembly, whereby a possibly occurring fault or a wear event giving rise to concern can also be localized very reliably so that ultimately the servicing and repair costs can be considerably lowered because the location of the fault or of the wear event can be determined e.g. automatically by a corresponding program-controlled machine and can be advised to a maintenance team and even the extent of the fault or of the wear can be advised to the maintenance team so that the correct and required measures can be taken immediately without any unnecessary time loss for the troubleshooting.

Assemblies which are accommodated at very inaccessible sites in the machine or machines which are installed at very inaccessible sites, e.g. deep beneath the sea, can thus also be monitored comfortably, possibly using the corresponding network technology, even online by a central servicing center.

In an embodiment of a method in accordance with the invention particularly important for practice, the signal generator and the sensor are integrated in a sensor module, whereby the total space which the signal generator and the sensor take up together can be minimized particularly easily so that the total sensor module can be installed in a particularly space-saving manner and also very simply at the assembly to be monitored.

It is also possible that the signal generator is also additionally, i.e. simultaneously, used as a sensor for the detection of the response signal, which allows a further miniaturization of the sensor module. A special embodiment of such a sensor module will be described further below in detail with reference to FIG. 1b.

As already mentioned, in this respect, the query signal is particularly preferably transmitted wirelessly by a suitable signal source e.g. via radio on a suitable carrier frequency, with naturally the response signal also being able to be transmitted correspondingly wirelessly to an evaluation unit for the evaluation and determination of the wear state.

As already described in detail further above, the signal generator and/or the sensor and/or the sensor module are produced at least partly from a suitable piezoelectric or piezoresistive material, in particular from a piezoelectric or piezoresistive monocrystal.

In this respect, the physical operating value which is monitored by the sensor module and from which the wear characteristic is ultimately derived from which the wear state can be recognized, can be any suitable physical value which is in connection with the wear state, in particular a pressure, a force, a torque, a flow of a fluid medium, very particularly preferably a temperature and/or a spatial or temporal distribution of these values.

In particular, but not only, when the assembly to be observed is a component or a subcomponent of a bearing, the signal generator and/or the sensor and/or the sensor module can be particularly advantageously provided in a rotating component or subcomponent of the assembly and/or at a stationary component or subcomponent of the assembly.

The method in accordance with the invention is in this respect generally suitable for evaluating the wear state of any assembly of a flow machine, but is in practice very particularly advantageously used for evaluating a wear state of a bearing arrangement of a flow machine, with the bearing arrangement particularly preferably being a mechanical shaft bearing comprising a rotatable shaft arranged in a stationary bearing, or also being able to be a tilting segment axial bearing comprising a tilting element arranged in a carrier body and having a plurality of segment bodies.

As likewise already mentioned, the monitoring and evaluation of the wear state can also be partly or fully automated so that the flow machine can be correspondingly controlled and/or regulated using the response signal.

The present invention further relates to an assembly of a flow machine, in particular to a bearing arrangement of a pump or turbine, with which assembly the method of the invention can be carried out. In this respect, a signal generator for generating a mechanical query signal as well as a sensor which is in contact with the assembly for detecting a response signal generated from the query signal are provided for determining a wear characteristic so that a wear characteristic can be determined from a change in the response signal and the wear state can be evaluated using the wear characteristic.

In an assembly in accordance with the invention, the signal generator and/or the sensor and/or the sensor modular is/are preferably, but not necessarily, provided in a rotating subcomponent and/or at a stationary subcomponent of the assembly, with the assembly in practice frequently being a bearing arrangement in the form of a mechanical shaft bearing comprising a rotatable shaft arranged in a stationary bearing saddle, with the signal generator and/or the sensor and/or the sensor module being provided, for example, at the rotatable shaft and/or at a bearing component of the stationary bearing saddle.

In another preferred embodiment, the assembly is a bearing arrangement in the form of a tilting segment axial bearing comprising a bearing segment arranged in a carrier body, with the signal generator and/or the sensor and/or the sensor module being provided at the carrier body and/or at the tilting element and/or at a segment body of the tilting element.

The invention moreover also relates to a flow machine, in particular to a pump or turbine, having an assembly in accordance with the present invention so that the wear state of an assembly of the flow machine can be evaluated in accordance with a method of the invention, in particular in the operating state.

BRIEF DESCRIPTION OF THE DRAWINGS

The invention will be explained in more detail in the following with reference to the drawing. There are shown in a schematic representation:

FIG. 1B is an embodiment of a wirelessly coupled sensor module;

FIG. 3B is a carrier body of the tilting segment axial bearing of FIG. 3a.

DETAILED DESCRIPTION OF THE EMBODIMENTS

A respective simple schematic embodiment of a sensor module will be explained briefly with reference to FIG. 1A and FIG. 1B for illustrating the functional principle of a sensor module suitable for the invention.

Figure 1A:
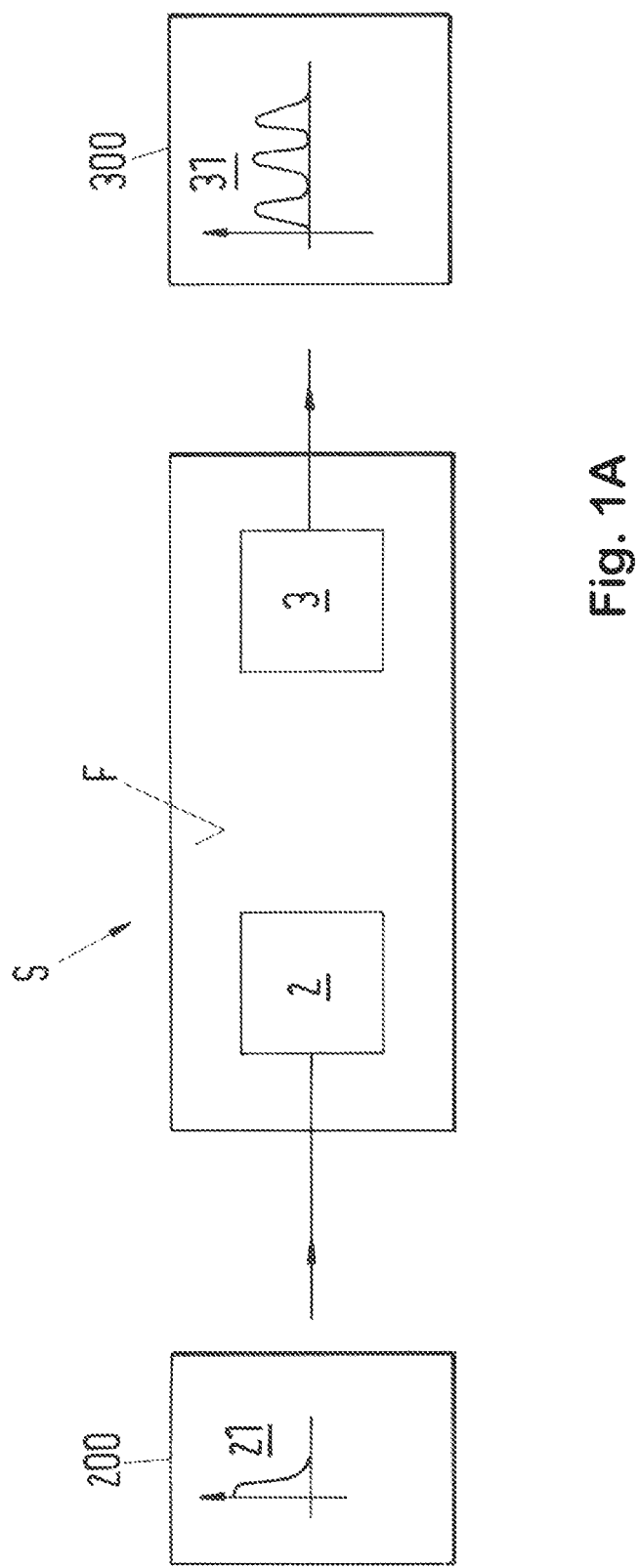
FIG. 1A is a simple schematic embodiment of a sensor module for carrying out the method in accordance with the invention.

Sensor modules in accordance with FIG. 1A and FIG. 1B respectively for carrying out a method in accordance with the invention are known as such from the prior art, for example under the keyword SAW sensors (surface acoustic wave sensors) and as such are also not directly the subject matter of the present invention.

The sensor module S in accordance with the very simple and highly schematically illustrated embodiment in accordance with FIG. 1A comprises a signal generator 2 which operates on a piezoelectric basis and which in the operating state generates a mechanical query signal 21 in the form of a mechanical surface acoustic wave having a predefinable signal shape on the sensor module S. The piezoelectric signal generator 2 is in this respect fed by the signal source 200 with a corresponding electrical or electromagnetic signal. The query signal 21 runs as a mechanical surface acoustic wave on the surface F of the sensor module S to the sensor 3. For example, the sensor module S experiences a small length change due to thermal expansion due to a temperature change which has had an effect on the sensor module S because, for example due to wear, the friction has increased in a bearing arrangement 11, 111, 112 to which the sensor module S is attached. This has the result that the sensor module S is no longer mechanically resonantly coordinated to the surface acoustic wave of the query signal, whereby the response signal 31 generated by the sensor 3 via the piezoelectric effect or the inverse piezoelectric effect is changed with respect to the query signal 21 in accordance with a characteristic pattern which depends on the type and the degree of mechanical detuning. The response signal 31 is supplied by the sensor 3 to an evaluation unit 300 with which then a wear characteristic can be determined from the change in the response signal 31, possibly with the assistance of previously carried out calibration measurements and the wear state can be evaluated using the wear characteristic.

FIG. 1B shows an embodiment of a sensor module S in which the signal generator 2 simultaneously operates as a sensor 3.

In the example of FIG. 1B, the query signal 21 is fed wirelessly via a radio connection in the form of an oscillating electromagnetic wave into an antenna T of the sensor module S and is supplied to the piezoelectric signal generator 2. The piezoelectric signal generator 2 generates via the piezoelectric effect or the inverse piezoelectric effect a mechanical surface acoustic wave which runs over the surface F of the sensor module S, is reflected at least in part at the reflection centers RZ and is thus reflected back to the signal generator 2, with the signal generator 2 now working as a sensor 3 while utilizing the piezoelectric effect or the inverse piezoelectric effect and again feeding the response signal 31 into the antenna T which wirelessly communicates the response signal 31 changed in a characteristic manner to an evaluation unit in which in turn the wear state can be determined or evaluated.

The basic operation of SAW sensors only briefly outlined above is well-known to the skilled person in all its different variants and can also be looked up in even more detail in the relevant technical literature.

Figure 2:
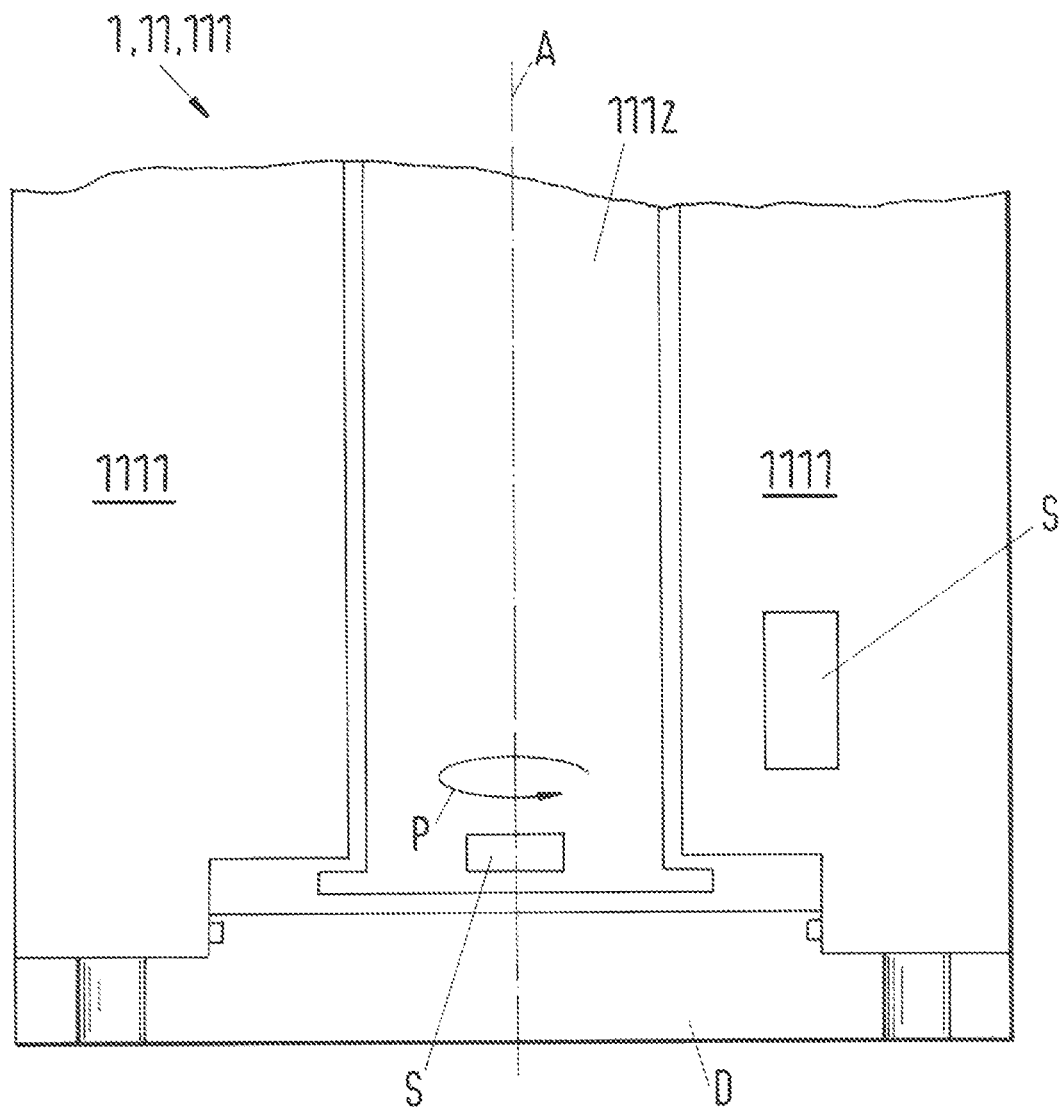
FIG. 2 is a mechanical shaft bearing in accordance with the invention.

FIG. 2 shows in a very schematic representation an assembly 1 known per se as a bearing arrangement 11 which is here designed in the form of a mechanical shaft bearing 111 in accordance with the invention and in which two sensor modules S are provided by way of example. One of the sensor modules S is in this respect provided in the static, non-rotating bearing saddle 1111, whereas a second sensor module S is positioned in the shaft 1112 rotating about the shaft axis A in the operating state. A particularly reliable determination of the wear state is inter alia possible and the location of the occurring wear phenomena can also be detected reliably and in good time by the use of two or even more sensor modules S in accordance with FIG. 2 which are preferably simultaneously provided at different positions of the assembly 1 in rotating components and in non-rotating components, as already described in detail above.

Figure 3A:
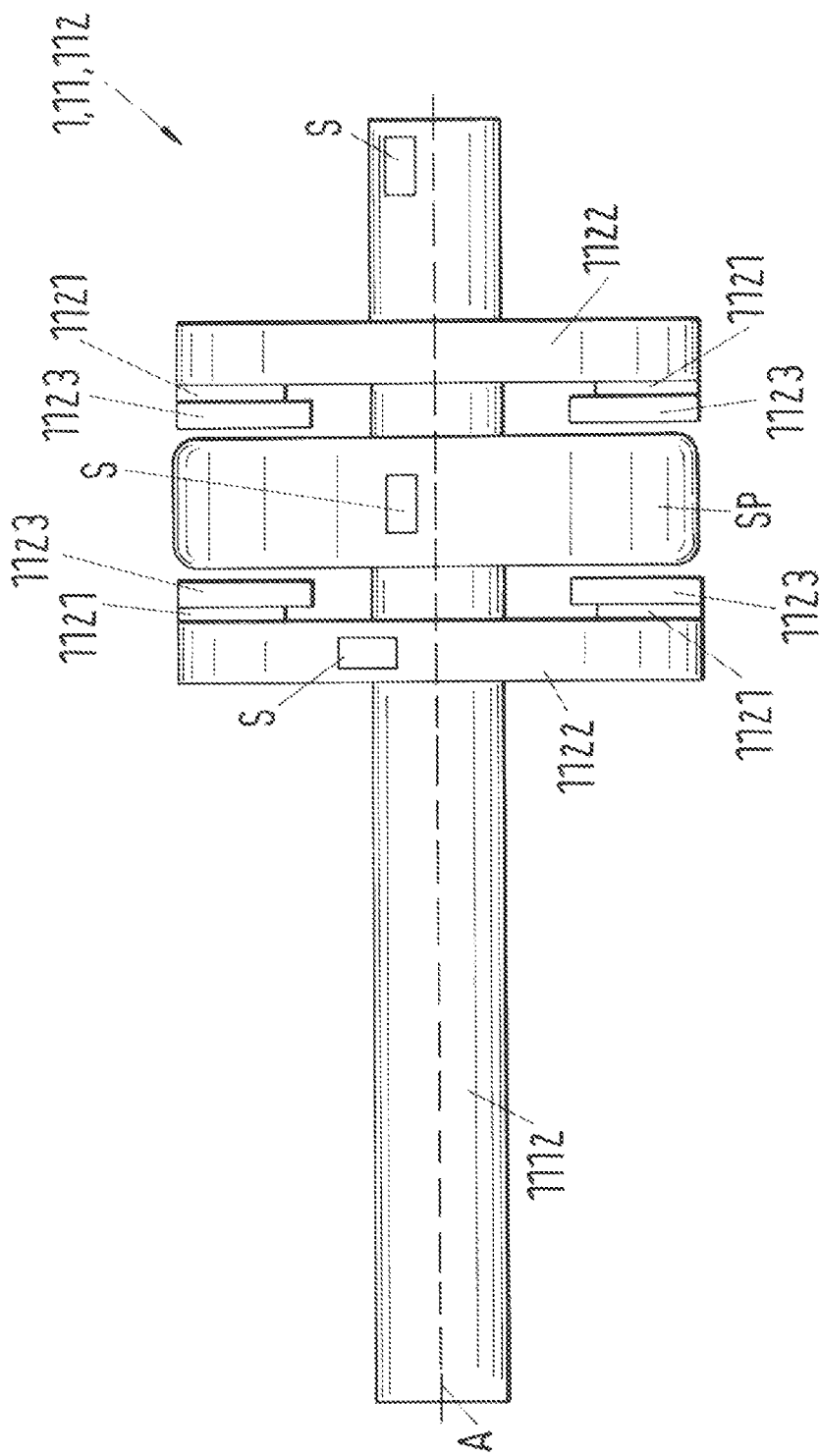
FIG. 3A is a tilting segment axial bearing in accordance with the invention.

FIG. 3A finally shows a tilting segment axial bearing 112 in accordance with the invention of a flow machine which is here specifically a pump. The tilting segment axial bearing 112 essentially differs from the tilting segment axial bearings known from the prior art in that in the tilting segment axial bearing 112 shown here sensor modules S are provided at static components and at rotating components of the tilting segment bearing 112.

The tilting segment axial bearing 112 of FIG. 3A comprises a carrier body 1122 having tilting elements 1121. A total of two carrier bodies 1122 are arranged concentrically around the pump shaft 1112 at the pump shaft 1112 which rotates about the shaft axis A in the operating state such that the tilting elements 1121 or the segment bodies 1123 of the two carrier bodies 1122 provided on the tilting elements 1121 are opposite one another. A thrust collar SP which transmits the axial pressure load to the segment bodies 1123 in a manner known per se is arranged between the two carrier bodies 1122.

Figure 3B:
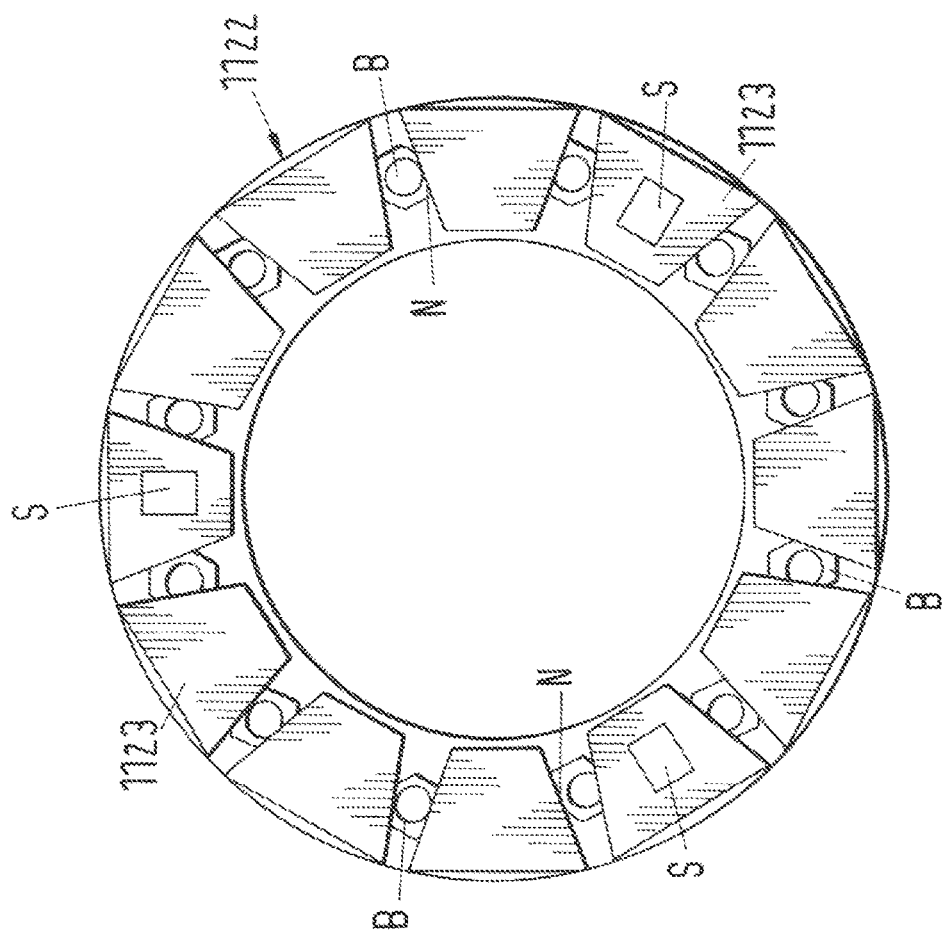

FIG. 3B shows one of the two carrier bodies 1122 of the tilting segment axial bearing 112 in accordance with FIG. 3A in somewhat more exact detail for illustration. The segment bodies 1123 are movably held at the carrier body 1122 by means of a fastening means B, for example by means of a nut which holds the segment body 1123 in a groove N at an outer margin of the segment body 1123.

In accordance with the present invention, in the specific embodiment of FIG. 3a and FIG. 3B, a plurality of sensor modules S are provided which, as can easily be recognized, are provided both at the pump shaft 1112 which rotates in the operating state and at the thrust collar SP, and in the present example even additionally at three segment bodies 1123 at the same spacing so that wear phenomena which occur can be determined ideally and in good time and can also be localized in the tilting segment bearing 112. In this respect, the sensor modules S are preferably, but not necessarily, worked into the corresponding component, e.g. are provided in a corresponding cut-out or e.g. are also molded into the material of the component so that the sensor modules S do not impede the interaction of the involved components in the operating state.

It is understood that all the embodiments of the invention described within the framework of this application are only to be understood as examples or by way of example and that the invention in particular, but not only, includes all suitable combinations of the described embodiments as well as simple further developments of the invention which likewise are easily obvious to the skilled person without any further inventive work.

The invention claimed is:

1. A method of evaluating a wear state of a component of a pump or a turbine, the method comprising:
generating a mechanical query signal in a form of a wave having a predefinable signal shape using a signal generator;
providing a sensor in contact with the component of the pump or the turbine;
detecting a response signal generated from the query signal using the sensor in contact with the component;
changing the response signal in dependence on a variation of a physical operating value of the component in accordance with a characteristic pattern; and
determining a wear characteristic of the component based on the change in the response signal and evaluating the wear state of the component based on the wear characteristic.

2. A method in accordance with claim 1, wherein the signal generator and the sensor are integrated in a sensor module.

3. A method in accordance with claim 1, wherein the signal generator is configured to operate as a sensor for the detection of the response signal.

4. A method in accordance with claim 1, further comprising
transmitting the query signal wirelessly to the signal generator by a signal source; or
transmitting the response signal wirelessly to an evaluation unit.

5. A method in accordance with claim 1, wherein at least one of the signal generator and the sensor comprises a piezoelectric material.

6. A method in accordance with claim 1, wherein the physical operating value is a temperature, a pressure, a force, a torque, a rotational speed, a flow of a fluid medium or a spatial or temporal distribution of these values.

7. A method in accordance with claim 6, wherein the sensor is configured to monitor the temperature or a time variation of the temperature.

8. A method in accordance with claim 1, wherein at least one of the signal generator and the sensor is disposed in a rotating subcomponent of the component or at a stationary subcomponent of the component.

9. A method in accordance with claim 1, wherein the component is a mechanical shaft bearing comprising a rotatable shaft arranged in a stationary bearing saddle.

10. A method in accordance with claim 1, wherein the component is a tilting segment axial bearing comprising a tilting element arranged in a carrier body and having a segment body.

11. A method in accordance with claim 1, wherein the pump or the turbine is controlled or regulated using the response signal.

12. A method in accordance with claim 1, wherein at least one of the signal generator and the sensor comprises a piezoelectric monocrystal.

13. A method in accordance with claim 1, wherein the sensor is a surface acoustic wave sensor.

14. A flow machine comprising:
an assembly including a bearing arrangement of a pump or turbine;
a signal generator configured to generate a mechanical query signal in a form of a wave, the signal generator disposed on the assembly; and
a surface acoustic wave sensor in contact with the assembly, the surface acoustic wave sensor being configured to detect a response signal generated from the query signal.

15. A flow machine in accordance with claim 14, wherein at least one of the signal generator and the sensor is disposed in a rotating subcomponent or at a stationary subcomponent of the assembly.

16. A flow machine in accordance with claim 14, wherein the assembly is a bearing arrangement in the form of a mechanical shaft bearing comprising a rotatable shaft arranged in a stationary bearing saddle, and at least one of the signal generator and the sensor is disposed at the rotatable shaft or at a bearing component of the stationary bearing saddle.

17. A flow machine in accordance with claim 14, wherein the assembly is a bearing arrangement in the form of a tilting segment axial bearing comprising a bearing segment arranged in a carrier body, and at least one of the signal generator and the sensor is disposed at the carrier body or at the tilting element or at a segment body of the tilting element.

* * * * *